United States Patent
Miyabe et al.

(10) Patent No.: US 6,648,924 B2
(45) Date of Patent: Nov. 18, 2003

(54) HAIR DYE COMPOSITION

(75) Inventors: Hajime Miyabe, Tokyo (JP); Kenichi Matsunaga, Tokyo (JP); Yukihiro Ohashi, Tokyo (JP); Shintaro Totoki, Tokyo (JP); Yoshinori Saito, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/825,954

(22) Filed: Apr. 5, 2001

(65) Prior Publication Data

US 2001/0052157 A1 Dec. 20, 2001

(30) Foreign Application Priority Data

Apr. 7, 2000 (JP) .................................. 2000-107186

(51) Int. Cl.$^7$ ................................. A61K 7/13
(52) U.S. Cl. .................. 8/405; 8/405; 8/406; 8/407; 8/409; 8/410; 8/411; 8/426; 8/437
(58) Field of Search ...................... 8/405, 407, 409, 8/410, 411, 426, 437, 406

(56) References Cited

U.S. PATENT DOCUMENTS

| | | | | |
|---|---|---|---|---|
| 3,741,982 A | * | 6/1973 | Fujino et al. | 206/326.15 |
| 3,812,107 A | | 5/1974 | Boehmke et al. | 260/260 |
| 3,897,418 A | | 7/1975 | Kuhlthau | 260/240 |
| 4,168,144 A | * | 9/1979 | Curry et al. | 8/10.1 |
| 4,168,264 A | | 9/1979 | Koller et al. | 260/165 |
| 4,251,656 A | | 2/1981 | Loew et al. | 542/417 |
| 4,344,879 A | | 8/1982 | Mohr et al. | 260/146 |
| 5,520,707 A | | 5/1996 | Lim et al. | 8/426 |
| 5,593,459 A | | 1/1997 | Gamblin | 8/539 |
| 5,733,343 A | * | 3/1998 | Mockli | 8/426 |
| 5,879,412 A | | 3/1999 | Rondeau et al. | 8/411 |
| 5,888,252 A | | 3/1999 | Moekli | 8/426 |
| 5,980,587 A | | 11/1999 | Samain | 8/426 |
| 5,993,490 A | * | 11/1999 | Rondeau et al. | 8/409 |
| 6,228,129 B1 | * | 5/2001 | de la Mettrie et al. | 8/401 |

FOREIGN PATENT DOCUMENTS

| | | |
|---|---|---|
| DE | 38 29 870 | 4/1989 |
| GB | 1 257 652 | 12/1971 |
| JP | 53-12931 | 2/1978 |
| JP | 54-7425 | 1/1979 |
| JP | 54-127433 | 10/1979 |
| JP | 56-76457 | 6/1981 |
| JP | 58-2204 | 1/1983 |
| JP | 6-271435 | 9/1994 |
| JP | 8-501322 | 2/1996 |
| JP | 8-507545 | 8/1996 |
| JP | 9-118832 | 5/1997 |
| JP | 10-502946 | 3/1998 |
| JP | 10-194942 | 7/1998 |

* cited by examiner

*Primary Examiner*—Mark Kopec
*Assistant Examiner*—Eisa Elhilo
(74) *Attorney, Agent, or Firm*—Oblon, Spivak, McClelland, Maier & Neustadt, P.C.

(57) ABSTRACT

Provided is a hair dye composition comprising a direct dye (1):

$$A-CR^1=N-NR^2-B\ X^- \qquad (1)$$

[wherein, A represents a group (2) or (3):

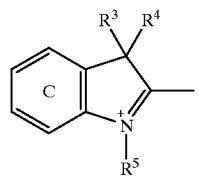

(2)

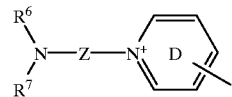

(3)

(in which, $R^3$, $R^4$ and $R^5$ each independently represents a (substituted) $C_{1-6}$ alkyl group, ring C may have a substituent or may by cyclocondensed with an aromatic ring, $R^6$ and $R^7$ each independently represents a (substituted) $C_{1-6}$ alkyl group, or may be coupled to form a heterocycle together with the adjacent nitrogen atom, Z represents a (substituted) $C_{1-4}$ divalent linear hydrocarbon group and ring D may be cyclocondensed with an aromatic ring), B represents a (substituted) aromatic group, $R^1$ represents H or a (substituted) $C_{1-6}$ alkyl group, $R^2$ represents H or a (substituted) $C_{1-6}$ alkyl group or a (substituted) aromatic group or may form a heterocycle together with the C atom of the aromatic ring B, and $X^-$ represents an anion]. This hair dye composition has markedly strong hair dyeing power and less color fade over time, and undergoes a smaller change in color tone of the dye even after storage.

1 Claim, No Drawings

HAIR DYE COMPOSITION

TECHNICAL FIELD

The present invention relates to a hair dye composition which has markedly high dyeing power, can impart the hair with a vivid color ranging from yellow to orange, has less color fade over time and undergoes a smaller change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when a cationic group is contained in an azo(—N═N—)-based conjugated system, they are unstable to an alkali agent or a reducing agent essentially contained in a permanent hair dye.

DISCLOSURE OF THE INVENTION

An object of the present invention is to provide a hair dye composition which has high hair dyeing power, has less color fade over time, and undergoes only a smaller change in color tone of the dye after storage, therefore has excellent stability.

The present inventors have found that a hair dye composition containing the below-described compound—which is known as a cationic dye for dying or printing therewith fiber materials, paper or leather and is, for example, described in Japanese Patent Application Laid-Open (Kokai) No. Sho 53-12931, Sho 54-7425, Sho 54-127433 or Sho 56-76457 is named as Basic Yellow 21 or Basic Yellow 28—can impart the hair with a vivid color ranging from yellow to orange without decomposing the dye upon hair drying, exhibits excellent light resistance, washing resistance, perspiration resistance, friction resistance and heat resistance, and undergoes a smaller change in the color tone of the dye after storage as compared with that rightly after preparation because the dye exists in the composition stably.

In one aspect of the present invention, there is thus provided a hair dye composition comprising, as a direct dye, a compound represented by the following formula (1):

[wherein, A represents a group of the following formula (2) or (3):

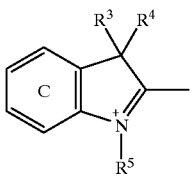

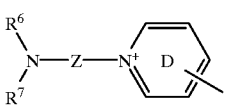

(in which, $R^3$, $R^4$ and $R^5$ each independently represents a $C_{1-6}$ alkyl group which may have a substituent, ring C may have a substituent or may be cyclocondensed with an aromatic ring, $R^6$ and $R^7$ each independently represents a $C_{1-6}$ alkyl group which may have a substituent, or may be coupled to form a heterocycle together with the adjacent nitrogen atom, Z represents a $C_{1-4}$ divalent linear hydrocarbon group which may have a substituent and ring D may be cyclocondensed with an aromatic ring)

B represents an aromatic group which may have a substituent, $R^1$ represents a hydrogen atom or a $C_{1-6}$ alkyl group which may have a substituent, $R^2$ represents a hydrogen atom or a $C_{1-6}$ alkyl group which may have a substituent or an aromatic group which may have a substituent, or may form a heterocycle together with the carbon atom of the aromatic ring B, and $X^-$ represents an anion.]

In another aspect of the present invention, there is also provided a hair dyeing method which comprises applying the above-described hair dye composition to the hair.

BEST MODE FOR CARRYING OUT THE INVENTION

In the formulas (1), (2) and (3), examples of the $C_{1-6}$ alkyl group as $R^1$, $R^2$, $R^3$, $R^4$, $R^5$, $R^6$ or $R^7$ include methyl, ethyl, propyl, isopropyl and cyclohexyl groups, which may each be substituted with an aryl, alkoxy, amino, hydroxyl or cyano group, or a halogen atom.

In the formula (1), examples of the substituent for the aromatic group as B or $R^2$ or for the ring C include alkyl, aryl, alkoxy, amino, dialkylamino, hydroxyl, cyano and nitro groups and halogen atoms, more specifically, methyl, ethyl, methoxy, ethoxy and diethylamino groups and chlorine and bromine atoms. The substituent for B may be cationic and a trimethylammonium ethoxy group may be mentioned as an example.

In the formula (3), examples of the $C_{1-4}$ divalent linear hydrocarbon group represented by Z include methylene, ethylene, trimethylene, propylene and butylene groups, which may each be substituted by an aryl, alkoxy, amino, hydroxyl or cyano group, or a halogen atom.

In the formula (1), examples of the anion as $X^-$ include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

Specific examples of the direct dye (1) to be used in the present invention include the following compounds:
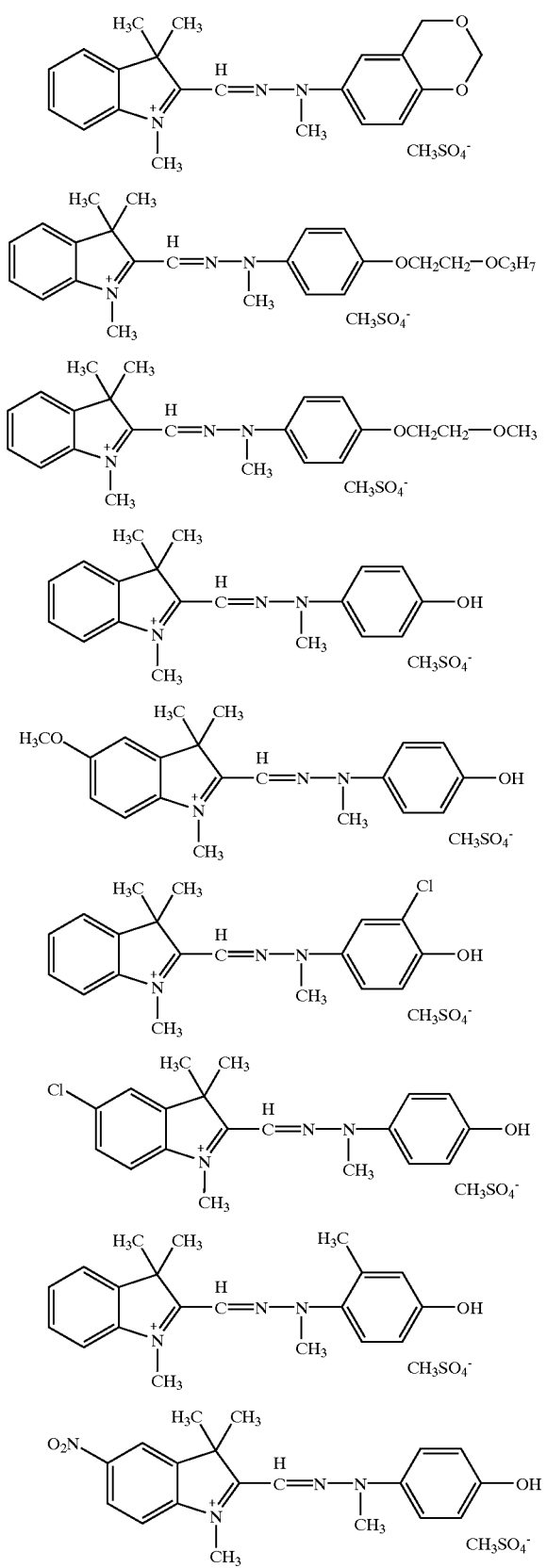
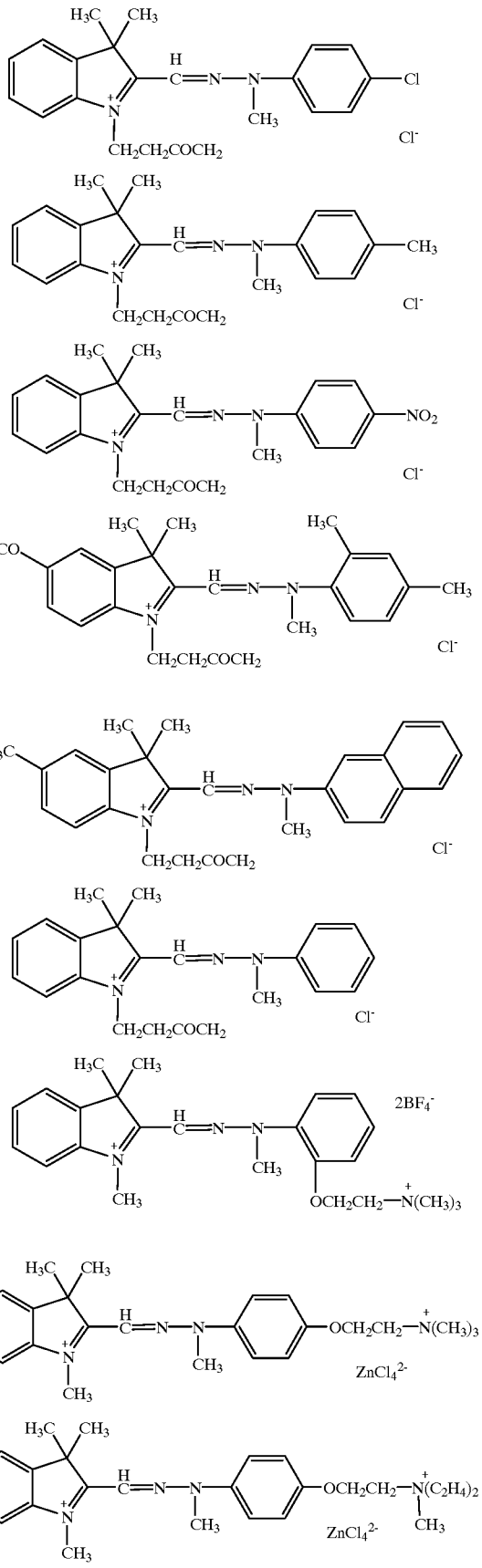

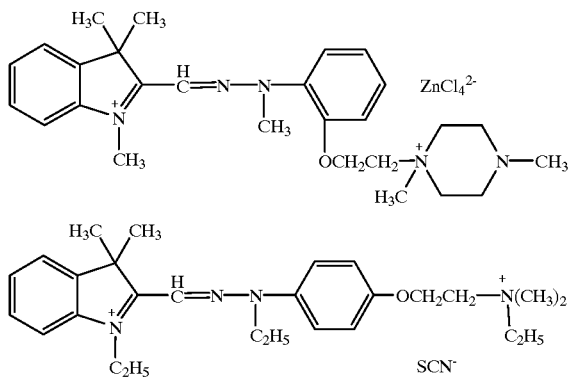

As the direct dye (1), one or more can be used. Alternatively, another direct dye can be used in combination. Combination of the direct dye (1) with red and blue dyes makes it possible to dye the hair with a deep and highly lustrous dark brown or black color.

Examples of the direct dye other than the direct dyes (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57(C.I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the parts when a two part or three part composition is employed; this will apply equally hereinafter). When another direct dye is added in combination, the content of it in total with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. The above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from $NH_2$—, NHR— and $NR_2$— groups (in which, R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives, p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole 6-hydroxyindole, 2,4-diamino-6-hydroxypyrimidine, 2,4,6-triaminopyrimidine, 2-amino-4,6-dihydroxypyrimidine 4-amino-2,6-dihydroxypyrimidine, 4,6-diamino-2-hydroxypyrimidine and 1,3-bis(2,4-diaminophenoxy)propane; and salts thereof.

As the developer or coupler, they may be used either singly or in combination. Each of the developer and coupler is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of the anionic component/ ion activity concentration of the cationic direct dye $(1) \leq 8$"

The term "ion activity concentration" as used herein means "molar concentration×ionic valence"

Addition of a polyol, polyol alkyl ether, cationic or amphoteric polymer or silicone to the hair dye composition of the present invention is preferred for uniform hair dyeing and improvement in cosmetic effects.

In addition to the above-described components, those ordinarily employed as a raw material for cosmetics can be added to the hair dye composition of the present invention within an extent not impairing the advantages of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first-part component containing an alkali agent and a second-part component containing an oxidizing agent, or a three-part composition containing, in addition to these two components, a powdery oxidizing agent such as persulfate. The direct dye (1) can be incorporated in either one or both of these components of the two-part or three-part composition. The one-part type is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the components when a two-part or three-part type is employed).

EXAMPLES

Compounds employed in the below-described examples are as follows:

Compound (a)

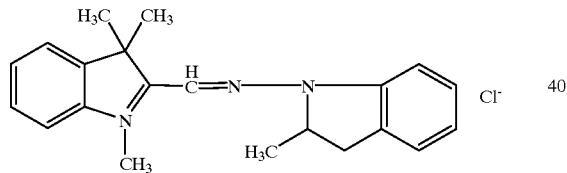

Compound (b)

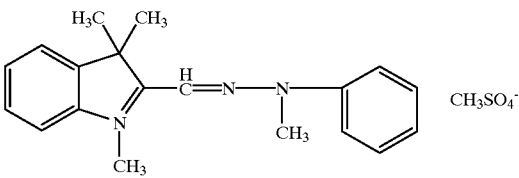

Compound (c)

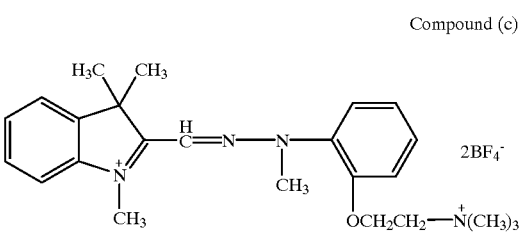

Compound (d)

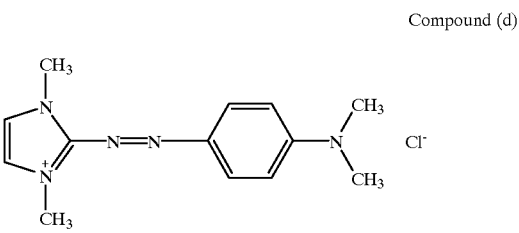

Examples 1 to 5

In a manner known per se in the art, hair dye compositions as shown in Table 1 were prepared.

TABLE 1

| (wt. %) | Examples | | | | |
| --- | --- | --- | --- | --- | --- |
| | 1 | 2 | 3 | 4 | 5 |
| Dye [Compound (a)] | 0.2 | | 0.15 | 0.1 | |
| Dye [Compound (b)] | | 0.5 | | 0.1 | 0.2 |
| Dye [Compound (d)] | | | 0.15 | 0.1 | 0.05 |
| Dye [Basic Blue 7] | | | 0.1 | 0.1 | |
| Ethanol | | 5 | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufquat 734" (trade name, product of ISP Japan) | 1 | 1 | | | |
| "Catinal LC100" (trade name, product of Toho Chemical Industry) | | | 1 | | 1 |
| "Polyether-modified silicone KF6005" (trade name, product of Shin-Etsu Chemical) | | | | | 0.4 |

TABLE 1-continued

| (wt. %) | Examples | | | | |
|---|---|---|---|---|---|
| | 1 | 2 | 3 | 4 | 5 |
| "Amodimethicone SM8702C" (trade name, product of Dow Corning Toray Silicone) | | | 1.5 | | |
| Monoethanolamine | | | 0.1 | | |
| Phosphoric acid | | Amount to adjust pH to 9 | | | |
| Perfume | | | q.s. | | |
| Water | | | balance | | |

Examples 6 to 9

In a manner known per se in the art, hair dye compositions as shown in Table 2 were prepared.

TABLE 2

| (wt. %) | Examples | | | |
|---|---|---|---|---|
| | 6 | 7 | 8 | 9 |
| 1st part | | | | |
| Dye [Compound (a)] | 0.2 | | 0.15 | 0.2 |
| Dye [Compound (b)] | | 0.1 | 0.15 | |
| Dye [Compound (d)] | | 0.1 | | 0.05 |
| Dye [Basic Blue 99] | | 0.3 | | |
| 28 wt. % Aqueous ammonia | | 5 | | |
| Monoethanolamine | | 2 | | |
| Propylene glycol | | 8 | | |
| Polyoxyethylene (20) isostearyl ether | | 24 | | |
| Polyoxyethylene (2) isostearyl ether | | 20 | | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | | 2 | |
| "Polyether modified silicone KF6005" (trade name; product of Shin-Etsu Chemical) | | | | 0.3 |
| Tetrasodium ethylenediaminetetraacetate | | | 0.1 | |
| Perfume | | | q.s. | |
| Ammonium chloride | | Amount to adjust pH to 10 | | |
| Water | | Balance | | |
| 2nd part | | | | |
| 35 wt. % Aqueous hydrogen peroxide | | 17.1 | | |
| Methylparaben | | 0.1 | | |
| Phosphoric acid | | Amount to adjust pH to 3.5 | | |
| Water | | Balance | | |

Examples 10 to 12

In a manner known per se in the art, hair dye compositions as shown in Table 3 were prepared.

TABLE 3

| (wt. %) | Examples | | |
|---|---|---|---|
| | 10 | 11 | 12 |
| 1st part | | | |
| Toluene-2,5-diamine | 1.9 | 1 | |
| Para-aminophenol | | | 1 |
| Resorcin | 2 | | |
| Para-amino-ortho-cresol | | | 1.1 |
| 2,4-Diaminophenoxyethanol | | 1.37 | |
| Dye [Compound (a)] | 0.05 | | |
| Dye [Compound (b)] | | 0.15 | |
| Dye [Compound (c)] | | | 0.1 |
| 28 wt. % Aqueous ammonia | | 5 | |
| Monoethanolamine | | 2 | |
| Propylene glycol | | 8 | |
| Polyoxyethylene (20) isostearyl ether | | 24 | |
| Polyoxyethylene (2) isostearyl ether | | 20 | |
| "Merquat 280" (trade name; product of Calgon Corp., a 35 wt. % aqueous solution) | 8 | | |
| "Polymer JR400" (trade name; product of Union Carbide) | | 0.5 | |
| "Amodimethicone SM8702C" (trade name; product of Dow Corning Toray Silicone) | | | 2 |
| Sodium sulfite | | 0.05 | |
| Ascorbic acid | | 0.5 | |
| Tetrasodium ethylenediaminetetraacetate | | 0.1 | |
| Perfume | | q.s. | |
| Ammonium chloride | | Amount to adjust pH to 10 | |
| Water | | Balance | |
| 2nd part | | | |
| 35 wt. % Aqueous hydrogen peroxide | | 17.1 | |
| Methylparaben | | 0.1 | |
| Phosphoric acid | | Amount to adjust pH to 3.5 | |
| Water | | Balance | |

Example 13

In a manner known per se in the art, the following hair dye composition was prepared.

| | (wt. %) |
|---|---|
| (First part) | |
| Para-aminophenol | 1 |
| Para-amino-ortho-cresol | 1.1 |
| Compound (a) | 0.1 |
| 28 wt. % Aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |

-continued

| | (wt. %) |
|---|---|
| Tetrasodium ethylenediaminetetraacetate | 0.1 |
| Perfume | q.s. |
| Ammonium chloride | Amount to adjust pH to 10 |
| Water | Balance |
| (Second part) | |
| 35 wt. % Aqueous hydrogen peroxide | 17.1 |
| Methylparaben | 0.1 |
| Phosphoric acid | Amount to adjust pH to 3.5 |
| Water | Balance |

What is claimed is:

1. A hair dyeing method which comprises applying a hair dye composition comprising, as a direct dye, a compound represented by the following formula (1):

 (1)

wherein, A represents a group of the following formula (2) or (3):

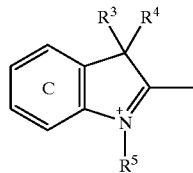 (2)

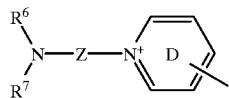 (3)

wherein, $R^3$, $R^4$ and $R^5$ each independently represents a $C_{1-6}$ alkyl group which may have a substituent, ring C may have a substituent or may be cyclocondensed with an aromatic ring, $R^6$ and $R^7$ each independently represents a $C_{1-6}$ alkyl group which may have a substituent, or may be coupled to form a heterocycle together with the adjacent nitrogen atom, Z represents $C_{1-4}$ divalent linear hydrocarbon group which may have a substituent and ring D may be cyclocondensed with an aromatic ring)

B represents an aromatic group which may have a substituent, $R^1$ represents a hydrogen atom or a $C_{1-6}$ alkyl group which may have a substituent, $R^2$ represents a hydrogen atom or a $C_{1-6}$ alkyl group which may have a substituent or an aromatic group which may have a substituent or may form a heterocycle together with the carbon atom of the aromatic ring B, and $X^-$ represents an anion;

to the hair in presence of an oxidation dye and an oxidizing agent which act for dyeing and bleaching simultaneously.

* * * * *